US012751759B2

(12) United States Patent
Kim et al.

(10) Patent No.: US 12,751,759 B2
(45) Date of Patent: Oct. 6, 2026

(54) HIGH FREQUENCY OUTPUT DEVICE AND INVASIVE TIP THEREFOR

(71) Applicant: WONTECH CO., LTD., Daejeon (KR)

(72) Inventors: Jong Won Kim, Seongnam (KR); Jung Hyun Kim, Seongnam (KR); Young Seok Seo, Sejong (KR); Jung Il Park, Seongnam (KR); Ye Chan Nam, Uiwang (KR)

(73) Assignee: WONTECH CO., LTD., Daejeon (KR)

( * ) Notice: Subject to any disclaimer, the term of this patent is extended or adjusted under 35 U.S.C. 154(b) by 140 days.

(21) Appl. No.: 18/913,911

(22) Filed: Oct. 11, 2024

(65) Prior Publication Data

US 2026/0069342 A1 Mar. 12, 2026

(30) Foreign Application Priority Data

Sep. 6, 2024 (KR) ........................ 10-2024-0121868

(51) Int. Cl.

*A61B 18/14* (2006.01)
*A61B 18/00* (2006.01)
*A61B 90/00* (2016.01)

(52) U.S. Cl.

CPC .............. *A61B 18/14* (2013.01); *A61B 90/03* (2016.02); *A61B 2018/00077* (2013.01); *A61B 2018/00083* (2013.01); *A61B 2018/0016* (2013.01); *A61B 2018/00184* (2013.01); *A61B 2018/0047* (2013.01); *A61B 2018/00702* (2013.01); *A61B 2018/143* (2013.01); *A61B 2018/1467* (2013.01); *A61B 2018/1475* (2013.01); *A61B 2090/034* (2016.02)

(58) Field of Classification Search

CPC ..... A61B 18/14; A61B 18/1477; A61B 90/03; A61B 2018/00077; A61B 2018/00083; A61B 2018/0016; A61B 2018/00184; A61B 2018/0047; A61B 2018/00702; A61B 2018/143; A61B 2018/1467; A61B 2018/1475; A61B 2090/034; A61B 2017/00747

USPC .......................................................... 606/41

See application file for complete search history.

(56) References Cited

U.S. PATENT DOCUMENTS

2019/0217080 A1* 7/2019 Moss .................. A61N 1/0502
2021/0128910 A1* 5/2021 Soden .................. A61M 37/00

(Continued)

FOREIGN PATENT DOCUMENTS

WO WO-2019032474 A1 * 2/2019 ........... A61N 1/0476

*Primary Examiner* — Beverly M Flanagan

(74) *Attorney, Agent, or Firm* — Harvest IP Law, LLP

(57) ABSTRACT

A high frequency output device and an invasive tip therefor are proposed, and the invasive tip includes a substrate, a needle array extending from a first surface of the substrate, one or more conductive pins extending from a second surface of the substrate, a bracket for supporting the substrate and guiding the one or more conductive pins, and a housing configured to accommodate the bracket inside thereof, have a plurality of through holes formed in a first end thereof opposite the first surface, and have a side wall formed to surround the needle array between the first end and a second end, the side wall having a shape of an inclined surface whose horizontal cross-sectional area decreases from a first point on the side wall to the first end, wherein the substrate includes wiring for electrically conductively connecting the one or more conductive pins to the needle array.

18 Claims, 9 Drawing Sheets

(56) References Cited

U.S. PATENT DOCUMENTS

| | | | | |
|---|---|---|---|---|
| 2022/0387092 | A1* | 12/2022 | Varshavsky | A61B 18/1402 |
| 2024/0245454 | A1* | 7/2024 | Kreindel | A61B 18/14 |
| 2025/0143779 | A1* | 5/2025 | Liang | A61N 1/02 |
| 2025/0375242 | A1* | 12/2025 | Lee | A61B 18/1477 |

* cited by examiner

HIGH FREQUENCY OUTPUT DEVICE AND INVASIVE TIP THEREFOR

CROSS REFERENCE TO RELATED APPLICATION

The present application claims priority to Korean Patent Application No. 10-2024-0121868, filed Sep. 6, 2024, the entire contents of which are incorporated herein for all purposes by this reference.

BACKGROUND OF THE INVENTION

Field of the Invention

The present disclosure relates to an invasive tip detachably attached to a handpiece of a high frequency output device and, more particularly, to an invasive tip provided with a mechanical structure capable of penetrating into the skin of a user so as to emit high-frequency energy, but capable of protecting needles from impacts or external forces during its operation.

Description of the Related Art

With the advancement of medicine, various devices for performing skin care by using various energy sources have become known. Among those devices, there is a high frequency output device that provides various effects such as improving skin elasticity and smoothing wrinkles by delivering high-frequency energy under the skin of a person to raise a temperature inside the skin and reorganize collagen layers.

Methods of treatment using high frequency output devices may include a non-invasive method in which a non-invasive high-frequency electrode is brought into contact with a skin surface and then high-frequency current is applied to the inside of the skin, and an invasive method in which high-frequency current is directly transmitted to the inside of the skin after a needle-shaped invasive electrode is inserted into the skin.

Among these methods, an invasive tip used in the invasive method uses microneedles each having a fine diameter in order to minimize pain and bleeding of a user during the treatment. Such microneedles have low durability due to their fine diameters, and have a risk that they may be easily broken or deformed during product delivery or operation.

In addition, in a case of being inserted into the skin too deeply during the treatment, the microneedles may cause more than expected pain and bleeding, so a method that may effectively limit a penetration depth of the microneedles is also required.

SUMMARY OF THE INVENTION

An objective of exemplary embodiments of the present disclosure for solving the technical problems therethrough is to provide an invasive tip having a mechanical structure capable of protecting microneedles from impacts or external forces during operation.

Another objective of the exemplary embodiments of the present disclosure for solving the technical problems therethrough is to provide an invasive tip capable of preventing excessive pain and bleeding during treatment by effectively limiting the insertion of microneedles too deeply into the skin.

The technical problems of the present disclosure are not limited to the above-mentioned technical problems, and other technical problems not described above will be clearly understood by those skilled in the art from the description of the claims.

According to the exemplary embodiments of the present disclosure for solving the above technical problems, there is provided an invasive tip including: a substrate; a needle array extending from a first surface of the substrate; one or more conductive pins extending from a second surface of the substrate; a bracket for supporting the substrate and guiding the one or more conductive pins; and a housing configured to accommodate the bracket inside thereof, the housing having a first end facing the first surface, a second end opposite to the first end, and a side wall formed to surround the needle array between the first end and the second end, the side wall having an inclination portion with a shape of an inclined surface whose horizontal cross-sectional area decreases from an inclination start position on the side wall to the first end, wherein the first end has a plurality of through holes formed therein, the plurality of through holes is formed to be aligned with the needle array, the bracket is configured to be raisable and lowerable within the housing, the needle array is exposed to an outside of the housing or accommodated within the housing by passing through the through holes as the bracket is raised or lowered, and a raised height of the bracket may be limited by the side wall, on which the inclined surface is formed, when the bracket is raised.

As one exemplary embodiment, the inclined surface of the inclined portion may be inclined toward inward a horizontal center of the invasive tip from the inclination start position along the side wall to the first end of the housing.

As one exemplary embodiment, the substrate may comprise wiring for electrically conductively connecting the one or more conductive pins to the needle array, and electrical energy provided to the one or more conductive pins may be distributed to the needle array via the wiring.

As one exemplary embodiment, the invasive tip may further include a cap combined with the housing so as to cover the first end of the housing, wherein when the cap is associated with the housing, a predetermined gap is formed between an outer surface of the first end of the housing and an inner surface of the cap.

As one exemplary embodiment, a protrusion jaw having a predetermined height may be formed on an edge of the first end of the outer surface of the housing, the protrusion jaw may come into contact with the cap to form the gap when the cap is associated with the housing.

As one exemplary embodiment, a step opposite to the protrusion jaw may be formed on the inner surface of the cap, and the protrusion jaw may come into contact with the cap via the step when the cap is associated with the housing.

As one exemplary embodiment, a cap may include one or more legs extending in a longitudinal direction thereof, one or more trench grooves may be formed in the side wall of the housing, and the one or more legs may be inserted into the one or more trench grooves so as to secure the cap to the housing when the cap is associated with the housing.

As one exemplary embodiment, a catch jaw with sawtooth protrusions may be formed at one position of each of the one or more legs such that each sawtooth protrusion is sequentially caught in the one or more trench grooves when the cap is detached from the housing.

As one exemplary embodiment, the one or more conductive pins may include: a first conductive pin positioned at a first point on the substrate; and a second conductive pin positioned at a second point diagonally opposite the first point on the substrate, wherein the first conductive pin may be electrically connected to one or more first needles in the needle array, and the second conductive pin may be electrically connected to one or more second needles different from the one or more first needles in the needle array.

As one exemplary embodiment, the first conductive pin and the second conductive pin may function as electrodes of the same polarity so that current may flow in the same direction.

As one exemplary embodiment, the first conductive pin and the second conductive pin may function as electrodes of opposite polarities, enabling current to flow in opposite directions from each other.

As one exemplary embodiment, the substrate may include: a first substrate to which the needle array is fixed; and a second substrate disposed adjacent to the first substrate, and an insulating layer may be inserted between the first substrate and the second substrate.

As one exemplary embodiment, a semiconductor chip may be mounted on the second substrate, the first substrate may have a first wiring routed therein, the second substrate may have a second wiring routed therein, and the one or more conductive pins may include: a first conductive pin electrically connected to the first wiring; and a third conductive pin electrically connected to the second wiring.

As one exemplary embodiment, the one or more conductive pins may further include a third conductive pin electrically connected to the first wiring routed in the first substrate; and a fourth conductive pin electrically connected to the second wiring routed in the second substrate.

As one exemplary embodiment, the first and third conductive pins, which are connected to the first substrate, may be positioned diagonally opposite to each other, and the second and fourth conductive pins, which are connected to the second substrate, may be located diagonally opposite to each other.

As one exemplary embodiment, the one or more conductive pins may be elastic.

As one exemplary embodiment, the invasive tip may further include an alignment plate formed with a hole therein and configured to support a bottom surface of the bracket, wherein the alignment plate may be fixed to the inside of the housing, and the bracket may be accommodated in a space between the alignment plate and the inner wall of the housing, the space being partitioned and defined by the alignment plate.

As one exemplary embodiment, the invasive tip may further include an elevation protrusion extending from a bottom surface of the bracket, wherein the elevation protrusion may extend toward the second end of the housing by passing through a hole of an alignment plate.

As one exemplary embodiment, a handpiece device comprises: an invasive tip; an electrical circuit for providing high frequency energy to the invasive tip; a pressing unit configured to generate a force to move the invasive tip in a up-and-down direction; a controller configured to control the high frequency energy transmitted to the invasive tip and up-and-down movement of the invasive tip, wherein the invasive tip includes: a substrate; a needle array extending from a first surface of the substrate; one or more conductive pins extending from a second surface of the substrate; a bracket for supporting the substrate and guiding the one or more conductive pins; and a housing configured to accommodate the bracket inside thereof, the housing having a first end facing the first surface, a second end opposite to the first end, and a side wall formed to surround the needle array between the first end and the second end, the side wall having a inclination portion with a shape of an inclined surface whose horizontal cross-sectional area decreases from an inclination start position on the side wall to the first end, wherein the first end has a plurality of through holes formed therein, the plurality of through holes is formed to be aligned with the needle array, the bracket is configured to be raisable and lowerable within the housing, the needle array is exposed to an outside of the housing or accommodated within the housing by passing through the through holes as the bracket is raised or lowered, and a penetration height of the needle array is limited by the side wall, on which the inclined surface is formed, when the needle array penetrates a person's skin.

According to the exemplary embodiments of the present disclosure for solving the above technical problems, there is provided a high frequency output device including: a main body for generating high frequency energy; and a handpiece for receiving the high frequency energy from the main body and transmitting the high frequency energy to an invasive tip, wherein the invasive tip may include: a substrate; a needle array extending from a first surface of the substrate; one or more conductive pins extending from a second surface of the substrate; a bracket for supporting the substrate and guiding the one or more conductive pins; and a housing configured to accommodate the bracket inside thereof, have a plurality of through holes formed in a first end thereof opposite the first surface, and have a side wall formed to surround the needle array between the first end and a second end, the side wall having a shape of an inclined surface whose horizontal cross-sectional area decreases from a first point on the side wall to the first end, the substrate may include wiring for electrically conductively connecting the one or more conductive pins to the needle array, electrical energy provided to the one or more conductive pins may be distributed to the needle array via the wiring, the plurality of through holes may be formed to be aligned with the needle array, the bracket may be configured to be raisable and lowerable within the housing, the needle array may be exposed to an outside of the housing or accommodated within the housing by passing through the through holes as the bracket is raised or lowered, and the handpiece may include: an electrical circuit for providing the high frequency energy to the one or more conductive pins; and a pressing unit for generating a mechanical force to raise or lower the substrate within the housing.

According to the exemplary embodiments of the present disclosure described above, the cap is allowed to combine with a tip end where microneedles are exposable, so that the microneedles may be prevented from being damaged by external forces. In this case, a predetermined gap (or space) is formed between the housing and the cap to prevent as much as possible the microneedles from colliding with and being damaged by the inner surface of the cap covered with the housing.

According to such a mechanical structure, even when the microneedles protrude out of the housing due to some shaking or external impacts generated during delivery, transportation, or storage of the invasive tip, the microneedles may be protected by the cap from damage.

In addition, the invasive tip according to the present disclosure is configured to provide the structure in which the microneedles are stably stored within the housing by accommodating the microneedles in the space partitioned by the housing and the alignment plate, and the side wall of the housing is manufactured in a shape having an inclined surface, so that when the invasive tip penetrates into the skin beyond a predetermined depth (i.e., when the needles are raised within the housing), the bracket around the microneedles is brought into contact with the side wall to limit a penetration depth of the microneedles (i.e., limiting a raised height of the bracket), so as not to allow no further penetration, thereby preventing excessive pain and bleeding from occurring during treatment.

In addition, the substrate to which the microneedles are soldered is manufactured in a structure of double substrates having a buffer film inserted therebetween so as to alleviate impacts when the invasive tip is operated. The buffer film is configured as an insulating layer so as to prevent electrical interference between each substrate, thereby enabling each substrate to perform electrical operations independently of each other.

Accordingly, the invasive tip may be designed in various forms, such as having the microneedles on an upper substrate and mounting a separate semiconductor chip on a lower substrate. Accordingly, various functional applications may be implemented, such as simultaneously performing operations of storing, processing, etc. of information through the semiconductor chip on the lower substrate while applying high-frequency output through the microneedles on the upper substrate.

The technical effects of the present disclosure are not limited to the above-mentioned effects, and other technical effects not described above will be clearly understood by those skilled in the art from the description of the claims.

DETAILED DESCRIPTION OF THE INVENTION

Figure 1:
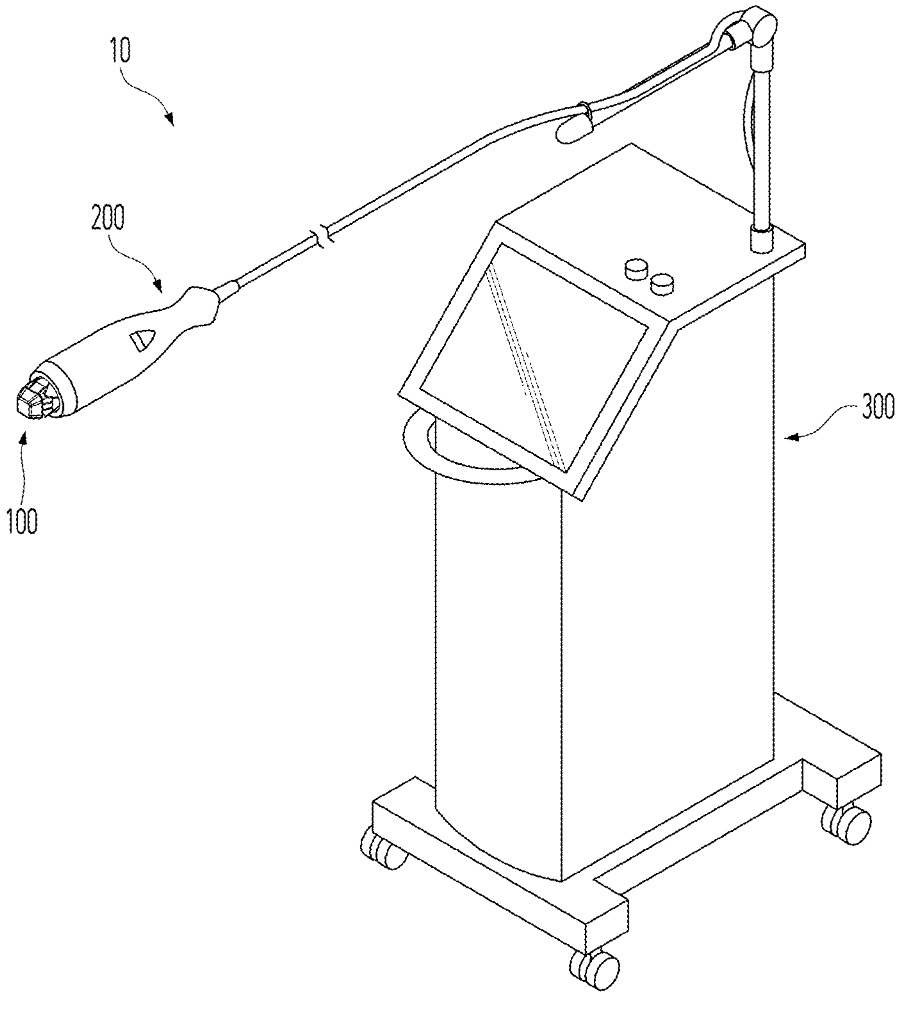
FIG. 1 is a perspective view illustrating a configuration of a high frequency output device according to an exemplary embodiment of the present disclosure.

Hereinafter, exemplary embodiments of the present disclosure are described with reference to the accompanying drawings. Advantages and features of the present disclosure and the methods of achieving the same will become apparent with reference to the exemplary embodiments described below in detail in conjunction with the accompanying drawings. However, the technical ideas of the present disclosure are not limited to the exemplary embodiments disclosed below, but may be implemented in a variety of different forms. These exemplary embodiments are provided only to facilitate understanding of the technical concepts of the present disclosure and to fully inform the scope of the present disclosure to those skilled in the art to which the present disclosure pertains. The technical ideas of present disclosure are only defined by the scope of the claims.

In adding reference numerals to the components of each drawing, it should be noted that the same reference numerals are used to refer to the same components as much as possible even if displayed on different drawings. In addition, in the following description of the present disclosure, detailed descriptions of known functions and components incorporated therein will be omitted if they are deemed to obscure the gist of the subject matter of the present disclosure.

Unless otherwise defined, all terms (including technical and scientific terms) used in the present description may be used in a sense that may be commonly understood by those skilled in the art. In addition, terms defined in the commonly used dictionary are not ideally or excessively interpreted unless otherwise specifically defined. The terminology used herein is for the purpose of describing particular exemplary embodiments only and is not intended to limit the exemplary embodiments of the present disclosure. In the present specification, the singular form also includes the plural form unless otherwise specified in the phrase.

Further, when describing the components of the present disclosure, terms such as first, second, A, B, A or B may be used. Since these terms are provided merely for the purpose of distinguishing the components from each other, these terms do not limit the nature, sequence, or order of the corresponding components. When a component is described as being "connected", "coupled", or "linked" to another component, that component may be directly connected, coupled, or linked to that other component. However, it should be understood that an additional component may also be present between the two, and those two components may be "connected", "coupled", or "linked" to each other via the additional component.

Hereinafter, some exemplary embodiments of the present disclosure will be described in detail with reference to the attached drawings.

FIG. 1 is a perspective view illustrating a configuration of a high frequency output device 10 according to an exemplary embodiment of the present disclosure. Referring to FIG. 1, the high frequency output device 10 may include an invasive tip 100, a handpiece 200, and a main body 300.

The main body 300 generates high-frequency energy (e.g., high-frequency current) of a predetermined frequency required for skin treatment. The frequency of the high-frequency energy may be determined differently depending on a patient's treatment purposes or treatment sites. For example, for skin treatment purposes, a frequency of high-frequency energy may be controlled in the range of 0.1 to 0.8 MHz.

The main body 300 may include an operation unit for controlling the power or frequency of the device 10. The main body 300 may further include a user interface for receiving a user input and displaying various information. The displayed information may include status of the device 10, patient information and operating the device 10. The user interface may be a touch screen.

The handpiece 200 is a component having the invasive tip 100 attached to an end part thereof, and is configured to provide high-frequency energy for skin treatment to the invasive tip 100. Specifically, the handpiece 200 receives the high-frequency energy from the main body 300, transmits the high-frequency energy to the invasive tip 100, and controls high-frequency output and operation of the invasive tip 100. The handpiece 200 is connected to the main body 300 at its proximal end and has the invasive tip 100 at its distal end.

As one exemplary embodiment, the handpiece 200 may control the movement of a needle array so that the needle array within the invasive tip 100 penetrates into the skin of a subject/patient during treatment. To this end, the handpiece 200 may be provided with a controller to control the movement of the needle array and a pressing unit (not shown) therein.

The pressing unit is a component that generates a mechanical force to move (e.g., raise or lower) the needle array within the invasive tip 100. For example, the mechanical force is applied to a substrate, to which the needle array is coupled, so as to push the substrate. Accordingly, the needle array is allowed to protrude out of the housing of the invasive tip 100, thereby penetrating into the skin of the patient.

When the needle array moves in a direction from the proximal end of the handpiece 200 toward the distal end, it is referred to as "raised." Conversely, when the needle array moves in an opposite direction, it is referred to as "lowered." The direction between the distal end and the proximal end of the handpiece 200 may be referred to as a longitudinal direction.

As one exemplary embodiment, the pressing unit may include a linear actuator such as a cylinder or a solenoid. Alternatively, the pressing unit may include a stepper motor or a servo motor. By way of having these components, the pressing unit may generate a force for up-and-down motion.

As one exemplary embodiment, an outer housing of the handpiece 200 may be provided with an operation button, and a user may turn the pressing unit on/off, manipulate a penetration depth of the needle array, or turn the high-frequency energy output of the invasive tip 100 on/off through the operation button. At the distal end of the handpiece 200, the outer housing of the handpiece 200 may include a distal end plate.

The invasive tip 100 includes the needle array 130, and through holes are formed at a first end of the housing. The through holes may be formed in the distal end plate. The needle array, by moving up-and-down in the longitudinal direction through the through holes, may be exposed to the outside or stored inside the housing. For example, during treatment, the needle array is moved out and exposed to the outside of the invasive tip 100 and penetrates into the patient's skin, and when the treatment is completed, the needle array is retracted into the invasive tip 100.

The invasive tip 100 has a structure detachably attachable to the handpiece 200, receives high-frequency energy from the handpiece 200, and emits the high-frequency energy to the inside of the skin through the needle array.

The detailed configuration and operation of the invasive tip 100 are described with reference to FIG. 2 and below.

Figure 2:
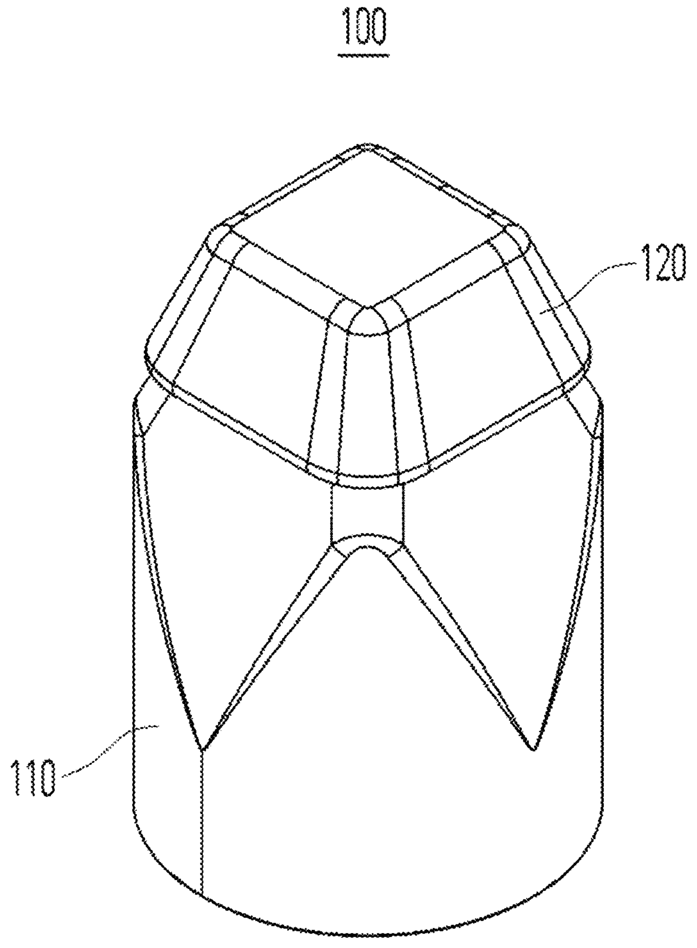
FIG. 2 is a perspective view illustrating an external appearance of an invasive tip mounted on a handpiece of a high frequency output device according to one exemplary embodiment of the present disclosure.

FIG. 2 is a perspective view illustrating an external appearance of an invasive tip mounted on a handpiece according to one exemplary embodiment of the present disclosure. Referring to FIG. 2, the invasive tip 100 may include a housing 110 and a cap 120 covering a first end of the housing 110.

The housing 110 is a component for providing a mechanical casing for the invasive tip 100 and protecting components of the invasive tip 100 from various external forces or impacts.

The cap 120 is a component that is detachably attached to the first end (i.e., distal end) of the housing 110. When attached to the housing 110, the cap 120 covers through holes provided in the first end of the housing 110 and prevents foreign substances from entering the inside of the invasive tip 100 through the through holes.

In addition, during processes of transporting, shipping, and storing the invasive tip 100, the needle array may unintentionally become exposed to the outside through the through holes of the invasive tip 100. In this case, attaching the cap 120 to the housing 110 allows the cap to function as a cover for the exposed needle array, thereby protecting the needle array from damages caused by external forces or impacts.

Meanwhile, when attached to the housing 110, the cap 120 may be attached such that a predetermined gap is provided between the inner surface of the cap 120 and the outer surface (i.e., a distal end surface) of the housing 110. In other words, the inner surface of the distal end of the cap 120 is spaced apart from an external surface of the distal end of the housing 110, when the cap 120 is associated to the housing 110. This configuration reduces the possibility of damage to the needle array that may collide with the inner surface of the cap 120 when the needle array is unintentionally exposed outside the through holes.

If there is no such gap between the housing 110 and the cap 120, the needle tips may come into contact with the inner wall of the cap 120 as soon as the needle array is exposed outside the through holes. This contact could result in the needles being damaged by collision with the cap 120.

In contrast, when there is the gap between the cap 120 and the housing 110, if the needle array is only partially exposed through the holes, the end part of the needle array remains within the gap and does not collide with the inner surface of the cap 120. This reduces likelihood of the needle array being damaged by collision with the cap 120.

Figure 3:
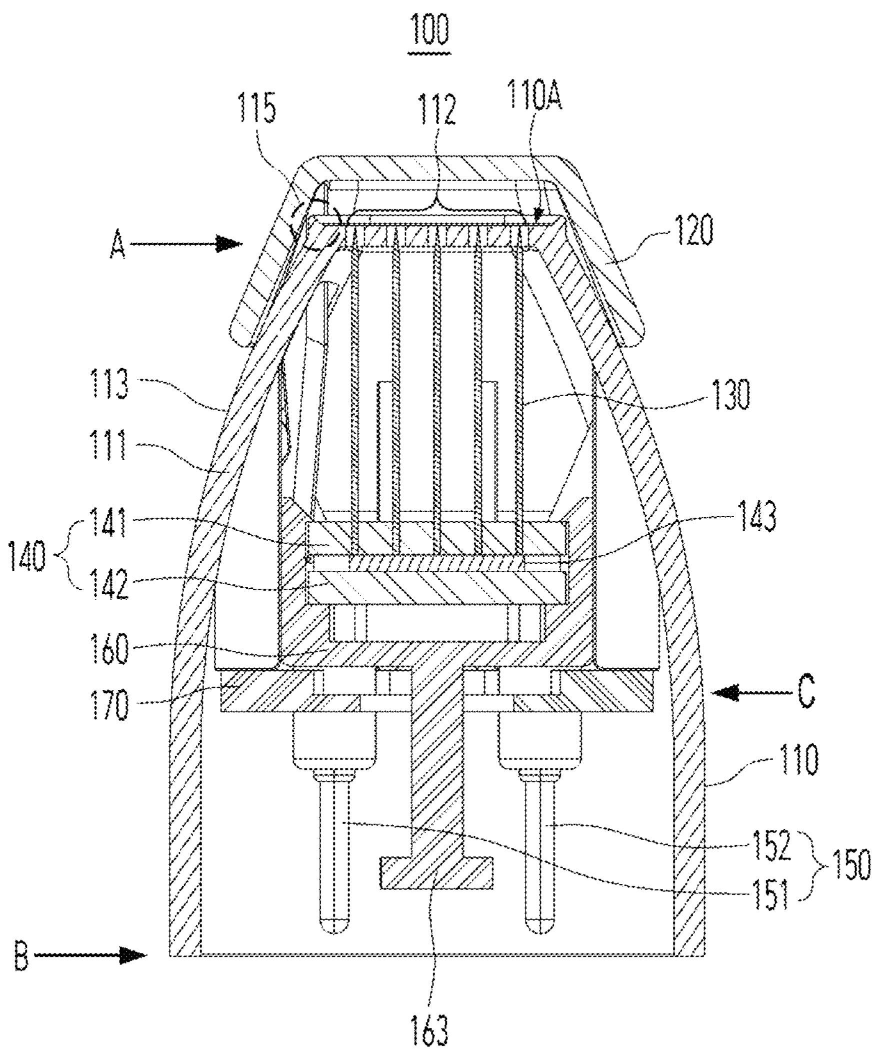
FIG. 3 is a vertical cross-sectional view illustrating a configuration of the invasive tip according to one exemplary embodiment of the present disclosure.

FIG. 3 is a vertical cross-sectional view illustrating a configuration of an invasive tip according to one exemplary embodiment of the present disclosure. The vertical cross-sectional view referred in FIG. 3 is based on a cross-sectional plane parallel to the longitudinal direction. Referring to FIG. 3, the invasive tip 110 may include a housing 110, a needle array 130, a substrate 140, conductive pins 150, a bracket 160, and an alignment plate 170.

The housing 110 accommodates the needle array 130, the substrate 140, the conductive pins 150, the bracket 160, and the alignment plate 170 therein, and has a plurality of through holes 112 formed at a first end (i.e., distal end) A thereof associated with a cap 120. In this case, the plurality of through holes 112 may be formed to be aligned with (i.e., to correspond to) the needle array 130.

In addition, the housing 110 may be provided with a side wall 111 formed between the first end A (i.e., distal end A) and a second end B (i.e., proximal end B) and configured to surround the needle array 130, the substrate 140, the conductive pins 150, the bracket 160, and the alignment plate 170.

The needle array 130 is a conductive needle array composed of a plurality of microneedles. When the needle array 130 is inserted into a human body, electric current flows through each of the plurality of microneedles, and high-frequency energy is emitted into the human body.

The substrate 140 is a component for supporting and/or fixing the needle array 130, and the needle array 130 extends upward from a first surface of the substrate 140 (i.e., an upper surface of the substrate based on FIG. 3) toward the through holes 112 of the housing 110.

The needle array 130 is fixedly coupled to the substrate 140 and may be electrically connected to wiring (not shown) formed on or in the substrate 140. For example, the needle array 130 may be coupled to the substrate 140 by soldering, with one or more holes formed along a wiring path on or in the substrate 140 and the needle array 130 inserted into the holes. This process creates an electrical connection between the wiring of the substrate 140 and the needle array 130.

The conductive pins 150 are one or more conductive pins 151 and 152, which are extending downward from a second surface (i.e., lower surface) of the substrate 140 (i.e., a bottom surface of the substrate based on FIG. 3). The second surface may be an opposite surface of the first surface where the needle array 130 is positioned.

The conductive pins 150 are electrically connected to the wiring formed on the substrate 140 and may receive high-frequency energy from the handpiece 200. The high-frequency energy transmitted from the handpiece 200 to the conductive pins 150 is distributed to each microneedle of the needle array 130 through the conductive pins 150 and the wiring sequentially along the electrical connection between the conductive pins 150, the wiring, and the needle array 130.

As one exemplary embodiment, each conductive pin 150 may be a spring pin connector capable of making elastic contact with an electrode pad provided in the handpiece 200. For example, each conductive pin 150 may be a pogo pin. Due to the elasticity of the conductive pin 150, the conductive pin 150 may remain in contact with an electrode pad provided in the handpiece 200 while the substrate 140 is raised or lowered.

The bracket 160 supports the substrate 140 by supporting the bottom surface of the substrate 140. The bracket 160 also guides each conductive pin 150. To this end, the bracket 160 may be provided with a reception groove for receiving the substrate 140 and/or a guide groove or guide hole for guiding each conductive pin 150. When the bracket 160 is assembled with the substrate 140, each conductive pin 150, which protrudes downward from a bottom surface of the substrate 140 may extend by passing through the bracket 160.

As one exemplary embodiment, the bracket 160 is configured to be raisable and lowerable within the housing 110 according to an operation of the pressing unit. When the bracket 160 is raised and lowered, the needle array 130 may move upward and be exposed to the outside of the housing 110 (that is, when the bracket is raised) or may retreat downward and be stored within the housing 110 (that is, when the bracket is lowered) by passing through the through holes.

The alignment plate 170 supports the bottom surface of the bracket 160. The alignment plate 170 may be formed with holes penetrating the alignment plate 170. The position of the holes may be, for example, a central part of the alignment plate 170. The elevation protrusion 163 may be formed by extending downward from a bottom surface of the bracket 160. The elevation protrusion may extend through the holes in the alignment plate 170 when assembled.

The alignment plate 170 may be fixedly coupled to the inside of the housing 110, and in this case, the needle array 130, the substrate 140, and/or the bracket 160 may be accommodated in a space partitioned (i.e., defined or surrounded) by the alignment plate 170 and an upper part of the housing 110, i.e., a space between the alignment plate 170 and the side wall 111 of the housing 110.

In this case, the components of the invasive tip 100, such as, the needle array 130, the substrate 140, and/or the bracket 160, which are internal components, are stably accommodated in the space partitioned by the alignment plate 170. They are not separated from this space even when there are significant impacts from the outside.

As one exemplary embodiment, the side wall 111 of the housing 110 may have a horizontal cross-sectional profile in the form of an inclined surface. The horizontal cross-section is based on a cross-sectional plane perpendicular to the longitudinal direction. According to the shape of such a side wall 111, a penetration depth of the microneedles (or the needle array) may be mechanically limited, thereby preventing excessive penetration causing pain or bleeding during treatment. This will be described in more detail.

In the present exemplary embodiment, the side wall 111 of the housing 110 may have a shape of an inclined surface 113 whose horizontal cross-sectional area decreases from an inclination start position C on the side wall up to the first end A where the through holes 112 are formed. The inclination start position C may be any one position on the side wall 111 between the first end (i.e., the distal end) and the second end (i.e., the proximal end) of the housing 110.

In other words, the side wall 111 of the housing 110 may be inclined inward toward a horizontal center of the invasive tip 100 from the inclination start position C along the side wall 111 to the distal end of the housing 110. Throughout the specification, the inward direction refers to a direction from the side wall 111 toward the center of the invasive tip 100 in a horizontal plane, and an outward direction refers to an opposite direction to the inward direction.

In this way, the side wall 111 of the housing 110 is manufactured in a shape having an inclined surface 113, so that when the needle array 130 penetrates into the skin beyond a predetermined depth (i.e., when the needle array is raised within the housing), the bracket 160 around the needle array 130 is brought into contact with a part of the inclined surface 113 of the side wall 111, so as not to allow no further progress, thereby limiting a penetration depth of the needle array 130. Accordingly, excessive pain and bleeding caused by the needle array 130 penetrating too deeply into the skin during the treatment may be effectively prevented through the use of a simple mechanical structure.

As one exemplary embodiment, the elevation of the needle array 130 may be controlled by the pressing unit (not shown) of the handpiece 200. To this end, an elevation protrusion 163 may be provided by protruding downward from the bottom surface of the bracket 160. The elevation protrusion 163 extends toward the second end B of the housing 110 through a hole formed in the alignment plate 170 and may be coupled to a driving shaft (not shown) extended from the pressing unit of the handpiece 200.

In this case, when the pressing unit pushes the driving shaft, the elevation protrusion 163 coupled to the driving shaft is pushed toward the first end A of the housing 110, and accordingly, the bracket 160 and the substrate 140 are raised, so that the needle array 130 is moved upward and exposed to the outside of the housing 110 through the through holes 112.

Conversely, when the pressing unit pulls the driving shaft, the elevation protrusion 163 coupled to the driving shaft is pulled toward the second end B of the housing 110, and accordingly, the bracket 160 and the substrate 140 are lowered, so that the needle array 130 retreats downward and is accommodated inside the housing 110.

As one exemplary embodiment, a protrusion jaw 115 having a predetermined height may be formed on an outer surface 110A of the first end A where the through holes 112 of the housing 110 are formed. The outer surface 110A of the housing 110 means the distal end surface of the housing 110. In this case, the protrusion jaw 115 may be formed at an outward edge or along the outward edge of the outer surface 110A extending upward further than its surroundings.

In this case, a step facing the protrusion jaw 115 may be formed on an inner surface of the cap 120 at a position corresponding to the protrusion jaw 115. When the cap 120 is associated with the first end A of the housing 110, the protrusion jaw 115 comes into contact with the step in the cap 120, thereby forming a predetermined gap between the inner surface of the cap 120 and the outer surface 110A of the housing 110. This will be described in more detail below in FIGS. 8A and 8B.

Figure 4A:
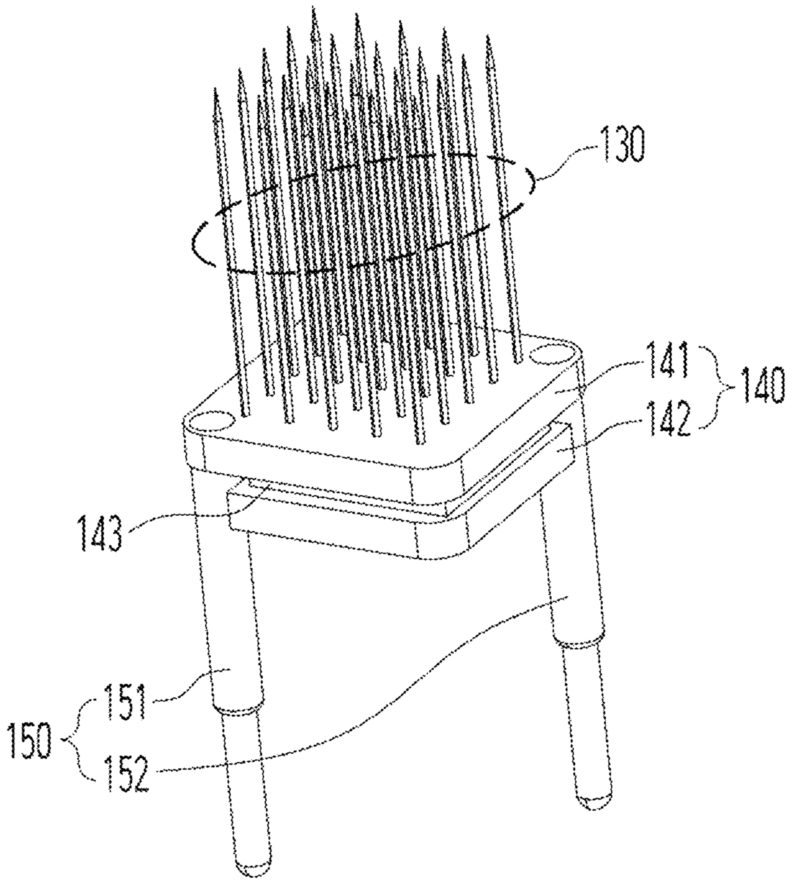
FIGS. 4A and 4B are views illustrating respective external appearances of a needle array, a substrate, and conductive pins according to one exemplary embodiment of the present disclosure.
Figure 4B:
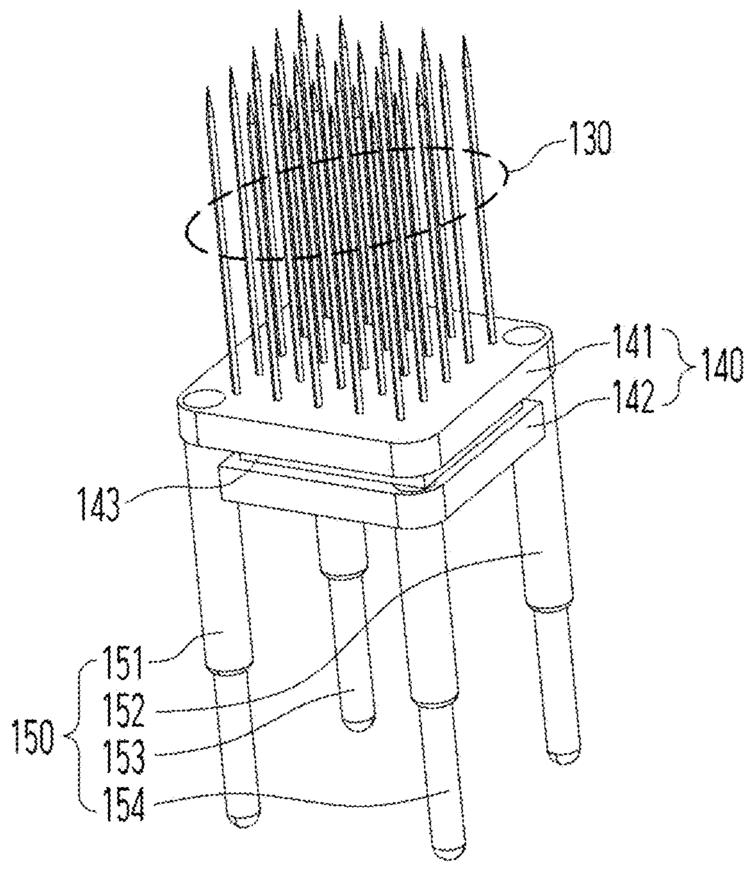

FIGS. 4A and 4B are views illustrating respective external appearances of a needle array 130, a substrate 140, and conductive pins 150 according to one exemplary embodiment of the present disclosure.

The needle array 130 is a conductive needle array including a plurality of microneedles. Each microneedle may have a diameter of approximately 20 μm. A portion of each needle from its tip to a position approximately 0.3 mm from the tip is configured with a conductive outer covering, so that high-frequency current may be allowed to flow into the skin of a person through the outer covering.

As one exemplary embodiment, each microneedle may be coated with an insulating material such as silicone in a part other than the conductive outer covering, thereby preventing high-frequency current from flowing to the sites other than treatment sites.

Meanwhile, in FIGS. 4A and 4B, the plurality of microneedles constituting the needle array 130 is arranged in a matrix form (i.e., arranged in rows and columns), but the scope of the present disclosure is not limited thereto. For example, the needle array 130 may also be configured in a form in which the plurality of microneedles is arranged along one or more concentric circles, and the number and arrangement of microneedles may be determined in various ways depending on treatment purposes and/or treatment sites.

As one exemplary embodiment, each of the plurality of microneedles is configured in the form of a hollow tube so that a drug supplied from the handpiece 200 may be allowed to be injected into a patient's skin through the hollow tubes of the microneedles.

The substrate 140 is a component for supporting the needle array 130. The needle array 130 may be coupled to the substrate 140 by way of soldering, and the needle array 130 may be electrically connected to the conductive pins 150 by the wiring inside the substrate 140.

In this case, electrical energy (e.g., high-frequency current) provided to the conductive pins 150 may be distributed to the needle array 130 through the wiring of the substrate 140.

Meanwhile, in FIGS. 4A and 4B, the substrate 140 is illustrated as having a square shape, but the scope of the present disclosure is not limited thereto. For example, the substrate 140 may be determined to have various shapes, such as a circular or regular polygonal shape, and sizes depending on the number of microneedles to be soldered and the internal space of the housing 110.

As one exemplary embodiment, the substrate 140 may be formed in a double structure in which a first substrate 141 and a second substrate 142 are overlayed with each other. In addition, a buffer film 143 may be inserted between the first substrate 141 and the second substrate 142.

In this way, when the substrate 140 is manufactured with the structure of double substrates having a buffer film 143 inserted therebetween, there is an advantage in that physical impacts transmitted to the substrate 140 and needle array 130 during the operation of the invasive tip 110 may be minimized.

As one exemplary embodiment, the buffer film 143 may be configured as an insulating layer, thereby supporting various applications of the invasive tip 110. This will be described in more detail.

For example, it may be implementable for an application using a separate semiconductor chip (not shown) mounted on a second substrate 142 while a needle array 130 is provided on a first substrate 141. In this case, while applying high-frequency output through the needle array 130 of the first substrate 141, other functions of storing, processing, etc. of information may be performed simultaneously through the semiconductor chip of the second substrate 142.

In this case, in order to prevent electrical interference between each of the substrates 141 and 142 and to enable the substrates 141 and 142 to perform respective electrical operations independently of each other, electrical insulation may be provided between two substrates 141 and 142 by forming the buffer film 143 with an insulating material. In this case, even though high-frequency current flows through the first substrate 141, since the second substrate 142 is insulated from the first substrate 141 by the buffer film 143, the second substrate 142 may perform its own function normally without being affected by the high-frequency current flowing through the first substrate 141.

As one exemplary embodiment, the buffer film 143 may include an insulating tape made of silicone, urethane, or elastomer.

Meanwhile, the double substrate structure of the substrate 140 may also contribute to optimize the internal space of the invasive tip 110. For example, in a case when the first substrate 141 and the second substrate 142 are separately provided at positions different from each other, a relatively larger volume within the invasive tip 110 may be required to contain the two separately-positioned substrates, and accordingly, there may occur various problems, such as the size of the invasive tip 110 needing to be increased.

In contrast, as in the present exemplary embodiments, when the substrate 140 is configured in the structure of double substrates having the buffer film 143 inserted therebetween, two substrates can be accommodated in almost the same space as that takes up when accommodating a single substrate, and thus the internal space of the invasive tip 110 may be efficiently utilized and the problem of insufficient internal space may be effectively overcome.

Meanwhile, the conductive pins 150 are configured to extend from the bottom surface of the substrate 140, and are connected to an electric circuit of the handpiece 200 so as to receive electrical energy from the handpiece 200.

As one exemplary embodiment, the conductive pins 150 may include two or more conductive pins that are distinct from each other. For example, the conductive pins 150 may include a first conductive pin 151 and a second conductive pin 152, which are electrically connected to the needle array 130. This will be described with reference to FIG. 4A.

In FIG. 4A, the first conductive pin 151 and the second conductive pin 152 may function as electrodes of the same polarity so that current may flow in the same direction. Alternatively, the first conductive pin 151 and the second conductive pin 152 may function as electrodes with different polarities, enabling current to flow in different directions from each other.

For example, in a case where the high frequency output device 10 operates in a monopolar mode, both the first conductive pin 151 and the second conductive pin 152 function as (+) electrodes, so that current in a direction toward the needle array 130 may flow through both electrodes.

In contrast, when the high frequency output device 10 operates in a bipolar mode, the first conductive pin 151 functions as a (+) electrode and the second conductive pin 152 functions as a (−) electrode, so that a current flowing in the direction toward the needle array 130 may flow through the first conductive pin 151, while a current flowing in the direction of coming from the needle array 130 may flow through the second conductive pin 152.

As one exemplary embodiment, the first conductive pin 151 and the second conductive pin 152 are provided at respective positions spaced apart from the first substrate 141. Each of the first conductive pin 151 and the second conductive pin 152 may be electrically connected to different sets of microneedles from among the plurality of microneedles in the needle array 130, through a first wiring (not shown) routed inside the first substrate 141.

To give a detailed example, the first conductive pin 151 may be positioned at a first point (e.g., a left corner based on FIGS. 4A and 4B) of the first substrate 141, and the second conductive pin 152 may be positioned at a second point (e.g., a right corner based on FIGS. 4A and 4B) facing the first point. In addition, The first conductive pin 151 may be electrically connected to one or more first microneedles (e.g., microneedles positioned in odd rows) among the plurality of microneedles in the needle array 130, while the second conductive pin 152 may be electrically connected to one or more second microneedles (e.g., microneedles positioned in even rows) that are distinct from the first microneedles among the plurality of microneedles in the needle array 130.

Under such a connection structure, when the high frequency output device 10 operates in the monopolar mode, high-frequency current provided through the first conductive pin 151 is distributed to each of the first microneedles, while high-frequency current provided through the second conductive pin 152 is distributed to each of the second microneedles. Accordingly, the high-frequency current may be supplied to the needle array 130 through two conductive pins 151 and 152, thereby enabling more current to be supplied quickly.

As another example, under such a connection structure, when the high frequency output device 10 operates in the bipolar mode, each of the first microneedles connected to the first conductive pin 151 functions as a (+) electrode, while each of the second microneedles connected to the second conductive pin 152 functions as a (−) electrode. In addition, during high-frequency current emission, high-frequency current is output through each of the first microneedles, passes through the inside of the skin, and is recovered through each o the second microneedles. In this way, effective implementation of bipolar mode is possible.

In this way, by electrically connecting two conductive pins 151 and 152 to the first substrate 141, two different modes of monopolar and bipolar may be implemented with the same configuration of the invasive tip 110.

Meanwhile, the conductive pins 150 may further include a third conductive pin 153 and/or a fourth conductive pin 154 electrically connected to the second substrate 142, in addition to the first and/or second conductive pins 151 and 152 electrically connected to the first substrate 141. This will be described with reference to FIG. 4B.

In FIG. 4B, the second substrate 142 may be equipped with a semiconductor chip as described above, and in this case, the third conductive pin 153 and the fourth conductive pin 154 may be electrically connected to the semiconductor chip through a second wiring (not shown) routed inside the second substrate 142. In this case, for example, the third conductive pin 153 may function as a (+) electrode that provides power to the semiconductor chip, while the fourth conductive pin 154 may function as a (−) electrode that provides ground to the semiconductor chip.

As one exemplary embodiment, one or more conductive pins electrically connected to the same substrate may be located at positions opposite to each other. For example, in a case where the first substrate 141 is configured in a square shape as shown in FIGS. 4A and 4B, the first conductive pin 151 and the second conductive pin 152 may be located at opposite corner positions diagonally facing each other, so as to ensure a sufficient separation distance therebetween, thereby minimizing mutual electrical interference.

Figure 5:
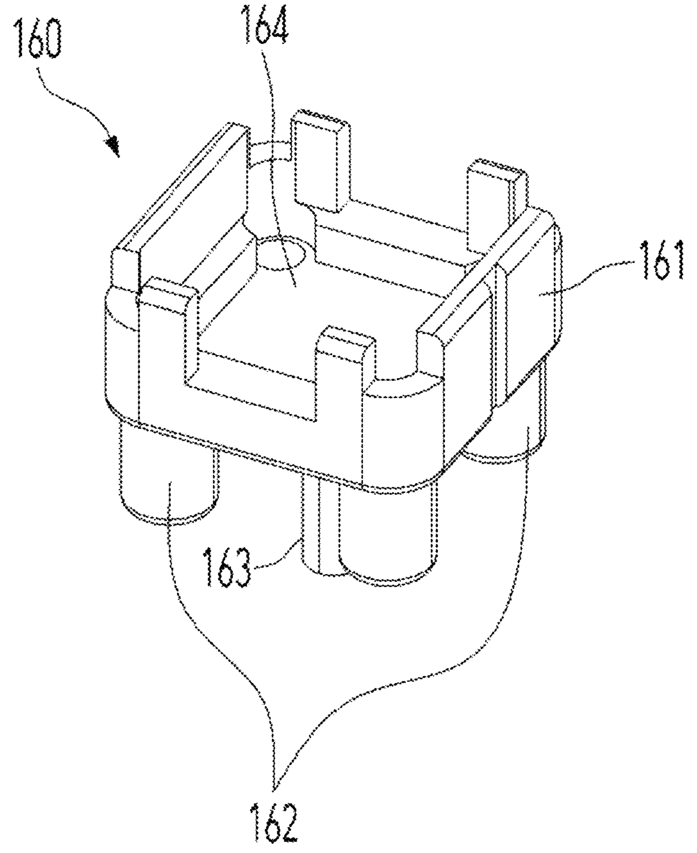
FIG. 5 is a view illustrating an external appearance of a bracket according to one exemplary embodiment of the present disclosure.

FIG. 5 is a view illustrating an external appearance of a bracket according to one exemplary embodiment of the present disclosure. Referring to FIG. 5, the bracket 160 may include: a bracket base 161 in which a receiving groove 164 for receiving a substrate 140 is formed; and guide holes or guide grooves 162 for guiding conductive pins 150.

As one exemplary embodiment, each of the guide holes or guide grooves 162 may be a component extending downward from the bottom surface of the bracket base 161 and having a predetermined height thereof. The conductive pins 150 may be inserted into the guide holes or guide grooves 162, and the conductive pins 150 may be aligned within a predetermined error range (e.g., within a diameter range of each guide hole or guide groove) by the guide holes or guide grooves 162.

As one exemplary embodiment, an elevation protrusion 163 for moving the bracket 160 may be provided on the bottom surface of the bracket base 161 by protruding downward. The elevation protrusion 163 is coupled to a pressing unit (or a driving shaft) of the handpiece 200 and moves the bracket base 161 coupled to the substrate 140. The elevation protrusion 163 may be configured in various forms that enable coupling with the pressing unit (or the driving shaft). The elevation protrusion 163 may protrude downward from a center of the bottom surface of the bracket base 161. However, in a case where the invasive tip 110 is manufactured with a structure in which the pressing unit (or the driving shaft) of the handpiece 200 can directly pressurize the bracket 160, the elevation protrusion 163 may be omitted.

Figure 6:
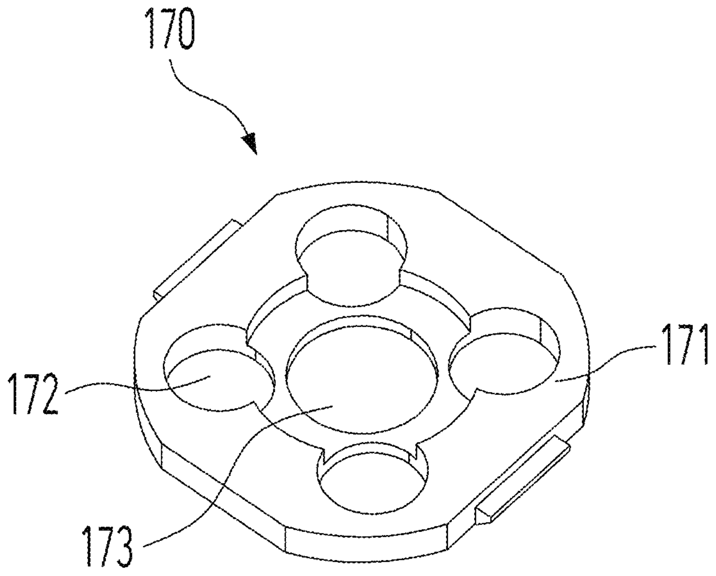
FIG. 6 is a view illustrating an external appearance of an alignment plate according to one exemplary embodiment of the present disclosure.

FIG. 6 is a view illustrating an external appearance of an alignment plate according to one exemplary embodiment of the present disclosure.

The alignment plate 170 includes an alignment plate base 171 for supporting the bottom surface of the bracket 160, and at least one or more holes 172 and 173 may be formed in the alignment plate base 171.

In this case, the holes 172 and 173 may include: the holes 172 for fixing or aligning the conductive pins 150; and the hole 173 for fixing or aligning the elevation protrusion 163.

In addition, the alignment plate 170 may be coupled to the housing 110, so as to partition and define a space in which the needle array 130, the substrate 140, and/or the bracket 160 are accommodated. In this way, during a process of detaching the invasive tip 100 from the handpiece 200, the bracket 160 coupled to the pressing unit (or the driving shaft) is prevented from coming out of the invasive tip 110 or the bracket 160 is prevented from being detached from inside the housing 110 because the alignment plate 170 supports the bracket 160 upward.

Figure 7:
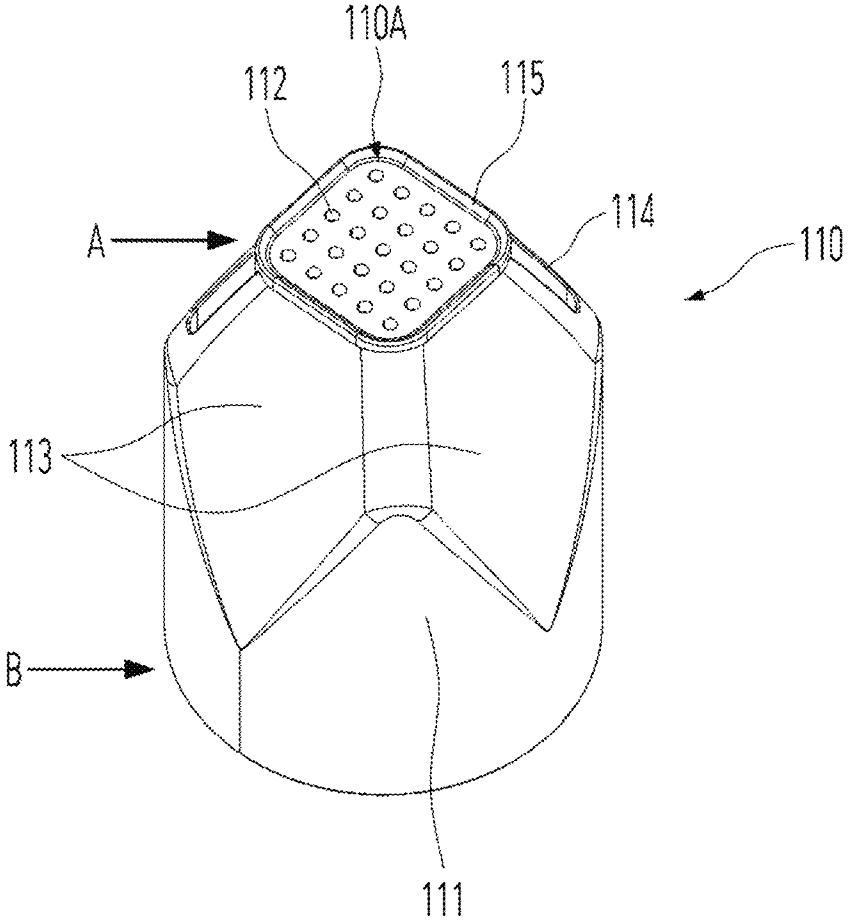
FIG. 7 is a view illustrating an external appearance of a housing according to one exemplary embodiment of the present disclosure.
Figure 8A:
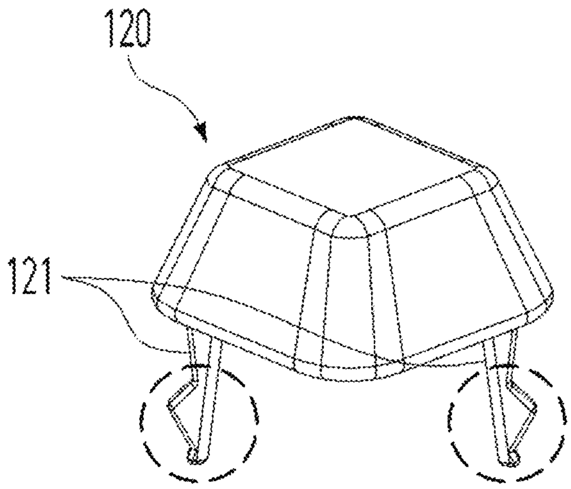
FIGS. 8A and 8B are views illustrating respective external appearances of a cap according to one exemplary embodiment of the present disclosure.
Figure 8B:
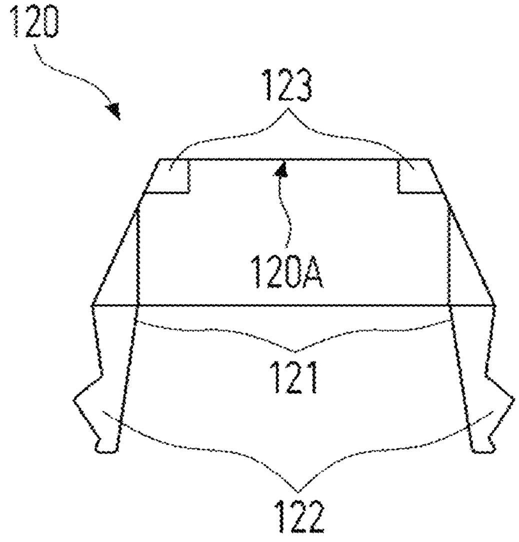

FIG. 7 is a view illustrating an external appearance of a housing according to one exemplary embodiment of the present disclosure. FIGS. 8A and 8B are views illustrating external appearances of a cap according to one exemplary embodiment of the present disclosure.

Referring to FIG. 7, the housing 110 may have a first end A (i.e., distal end A) thereof at which a plurality of through holes 112 through which a needle array 130 passes is formed. The housing 110 may have a second end B (i.e., proximal end B) thereof in an open shape.

A portion of the side wall 111 of the housing 110 may have a shape of an inclined surface 113 whose horizontal cross-sectional area decreases from inclination start position C between the first end A and the second end B to the first end A where the through holes 112 are formed. Accordingly, when the needle array 130 is raised upward at a predetermined level, a bracket 160 comes into contact with the inclined surface 113 of the side wall 111, so that the needle array 130 may be no longer raised, thereby preventing the needle array 130 from penetrating too deeply into the skin.

Meanwhile, as described above, a cap 120 is configured to be detachably attached to the housing 110, and the cap 120 may be configured to cover the first end A of the housing 110, in which the through holes 112 are formed, when the cap 120 is attached to the housing 110.

As one exemplary embodiment, the cap 120 may include one or more legs 121 extending in the longitudinal direction, and a catch jaw 122 may be formed at one position (e.g., a lower distal end) of each of the one or more legs 121. In addition, one or more trench grooves 114 may be formed in the side wall 111 of the housing 110, so that when the cap 120 is combined with the housing 110, catch jaws 122 of the one or more legs are inserted into the trench grooves 114, thereby allowing the cap 120 to be more firmly fixed to the housing 110.

As one exemplary embodiment, each catch jaw 122 may be an I-shaped protrusion (i.e., a straight-form protrusion) corresponding to the shape of each trench groove 114, or a sawtooth protrusion as shown in FIG. 8A. In a case where each catch jaw 122 is the sawtooth protrusion, when the cap 120 is detached from the housing 110, respective sawtooth parts are sequentially caught in the trench grooves 114 so that the cap 120 may be more firmly fixed to the housing 110.

As one exemplary embodiment, the protrusion jaw 115 may be formed on the outer surface 110A of the first end A, protruding upward at an edge of the outer surface 110A and having a predetermined height in the longitudinal direction. In addition, corresponding to this, the step 123 may be formed in one area of an inner surface 120A of the cap 120 as shown in FIG. 8B.

Accordingly, when the cap 120 is attached to the housing 110, the protrusion jaw 115 and the step 123 come into contact with each other, so that a gap may be stably formed between the housing 110 and the cap 120. In this case, by adjusting the height of the protrusion jaw 115 or the step 123, the size of the gap provided when the cap 120 is attached to the housing 110 may be controlled.

Although the exemplary embodiments of the present disclosure have been described above with reference to the accompanying drawings, it will be understood that those skilled in the art to which the present disclosure pertains may implement the present disclosure in other various forms as well without departing from the technical spirit or essential features thereof. Also, it is noted that any one feature of an embodiment of the present disclosure described in the specification may be applied to another embodiment of the present disclosure. Similarly, the present invention encompasses any embodiment that combines features of one embodiment and features of another embodiment. Therefore, the exemplary embodiments described above are to be understood in all respects as illustrative and not restrictive. The scope of protection of the present disclosure should be interpreted by the following claims, and all technical ideas within the scope equivalent thereto should be construed as being included in the scope of rights of the technical ideas defined by the present disclosure.

What is claimed is:

1. An invasive tip comprising:

a substrate;

a needle array extending from a first surface of the substrate;

one or more conductive pins extending from a second surface of the substrate;

a bracket for supporting the substrate and guiding the one or more conductive pins; and a housing configured to accommodate the bracket inside thereof, the housing having a first end facing the first surface, a second end opposite to the first end, and a side wall formed to surround the needle array between the first end and the second end, the side wall having an inclination portion with a shape of an inclined surface whose horizontal cross-sectional area decreases from an inclination start position on the side wall to the first end, wherein the first end has a plurality of through holes formed therein, the plurality of through holes is formed to be aligned with the needle array, the bracket is configured to be raisable and lowerable within the housing, the needle array is exposed to an outside of the housing or accommodated within the housing by passing through the through holes as the bracket is raised or lowered, and a penetration height of the needle array is limited by the side wall, on which the inclined surface is formed, when the needle array penetrates a person's skin, wherein the substrate comprises:

a first substrate to which the needle array is fixed; and a second substrate disposed adjacent to the first substrate, and an insulating layer is inserted between the first substrate and the second substrate.

2. The invasive tip of claim 1, wherein the inclined surface of the inclined portion is inclined toward a horizontal center of the invasive tip from the inclination start position along the side wall to the first end of the housing.

3. The invasive tip of claim 1, wherein the substrate comprises wiring for electrically conductively connecting the one or more conductive pins to the needle array, electrical energy provided to the one or more conductive pins is distributed to the needle array via the wiring.

4. The invasive tip of claim 3, further comprising:

a cap combined with the housing so as to cover the first end of the housing, wherein when the cap is associated with the housing, a predetermined gap is formed between an outer surface of the first end of the housing and an inner surface of the cap.

5. The invasive tip of claim 4, wherein a protrusion jaw having a predetermined height is formed on an edge of the outer surface of the first end of the housing, the protrusion jaw is configured to come into contact with the cap to form the gap when the cap is associated with the housing.

6. The invasive tip of claim 5, wherein a step opposite to the protrusion jaw is formed on the inner surface of the cap, the protrusion jaw is configured to come into contact with the cap via the step when the cap is associated with the housing.

7. The invasive tip of claim 1, wherein a cap comprises one or more legs extending in a longitudinal direction thereof, one or more trench grooves are formed in the side wall of the housing, and the one or more legs are inserted into the one or more trench grooves so as to secure the cap to the housing when the cap is associated with the housing.

8. The invasive tip of claim 7, wherein a catch jaw with sawtooth protrusions is formed at one position of each of the one or more legs such that each sawtooth protrusion is sequentially caught in the one or more trench grooves when the cap is detached from the housing.

9. The invasive tip of claim 1, wherein the one or more conductive pins comprise:

a first conductive pin positioned at a first point on the substrate; and a second conductive pin positioned at a second point diagonally opposite to the first point on the substrate, wherein the first conductive pin is electrically connected to one or more first needles in the needle array, and the second conductive pin is electrically connected to one or more second needles different from the one or more first needles in the needle array.

10. The invasive tip of claim 9, wherein the first conductive pin and the second conductive pin are configured to function as electrodes of the same polarity so that current may flow in the same direction.

11. The invasive tip of claim 9, wherein the first conductive pin and the second conductive pin are configured to function as electrodes of opposite polarities, enabling current to flow in opposite directions from each other.

12. The invasive tip of claim 1, wherein a semiconductor chip is mounted on the second substrate, the first substrate has a first wiring routed therein, the second substrate has a second wiring routed therein, and the one or more conductive pins comprises:

a first conductive pin electrically connected to the first wiring routed in the first substrate; and a second conductive pin electrically connected to the second wiring routed in the second substrate.

13. The invasive tip of claim 12, wherein the one or more conductive pins further comprises:

a third conductive pin electrically connected to the first wiring routed in the first substrate; and a fourth conductive pin electrically connected to the second wiring routed in the second substrate.

14. The invasive tip of claim 13, wherein the first and third conductive pins, which are connected to the first substrate, are positioned diagonally opposite to each other, and the second and fourth conductive pins, which are connected to the second substrate, are located diagonally opposite to each other.

15. The invasive tip of claim 1, wherein the one or more conductive pins are elastic.

16. An invasive tip comprising:

a substrate;

a needle array extending from a first surface of the substrate;

one or more conductive pins extending from a second surface of the substrate;

a bracket for supporting the substrate and guiding the one or more conductive pins;

a housing configured to accommodate the bracket inside thereof, the housing having a first end facing the first surface, a second end opposite to the first end, and a side wall formed to surround the needle array between the first end and the second end, the side wall having an inclination portion with a shape of an inclined surface whose horizontal cross-sectional area decreases from an inclination start position on the side wall to the first end, wherein the first end has a plurality of through holes formed therein; and an alignment plate formed with a hole therein and configured to support a bottom surface of the bracket, wherein the plurality of through holes is formed to be aligned with the needle array, the bracket is configured to be raisable and lowerable within the housing, the needle array is exposed to an outside of the housing or accommodated within the housing by passing through the through holes as the bracket is raised or lowered, and a penetration height of the needle array is limited by the side wall, on which the inclined surface is formed, when the needle array penetrates a person's skin; and wherein the alignment plate is fixed to the inside of the housing, and the bracket is accommodated in a space between the alignment plate and the inner wall of the housing, the space being partitioned and defined by the alignment plate.

17. The invasive tip of claim 1, further comprising:

an elevation protrusion extending from a bottom surface of the bracket, wherein the elevation protrusion extends toward the second end of the housing by passing through a hole of an alignment plate.

18. A high frequency output device comprising:

a main body for generating high frequency energy; and a handpiece for receiving the high frequency energy from the main body and transmitting the high frequency energy to an invasive tip, wherein the invasive tip comprises:

a substrate;

a needle array extending from a first surface of the substrate;

one or more conductive pins extending from a second surface of the substrate;

a bracket for supporting the substrate and guiding the one or more conductive pins; and a housing configured to accommodate the bracket inside thereof, the housing having a first end facing the first surface, a second end opposite to the first end, and a side wall formed to surround the needle array between the first end and the second end, the side wall having an inclination portion with a shape of an inclined surface whose horizontal cross-sectional area decreases from an inclination start position on the side wall to the first end, wherein he first end has a plurality of through holes formed therein, the plurality of through holes is formed to be aligned with the needle array, the bracket is configured to be raisable and lowerable within the housing, the needle array is exposed to an outside of the housing or accommodated within the housing by passing through the through holes as the bracket is raised or lowered, wherein the substrate comprises:

a first substrate to which the needle array is fixed; and a second substrate disposed adjacent to the first substrate, and an insulating layer is inserted between the first substrate and the second substrate, and the handpiece comprises:

an electrical circuit for providing the high frequency energy to the one or more conductive pins; and a pressing unit for generating a mechanical force to raise or lower the substrate within the housing.

* * * * *